United States Patent
Kondo et al.

(10) Patent No.: US 10,281,591 B2
(45) Date of Patent: May 7, 2019

(54) CERAMIC SCINTILLATOR ARRAY, X-RAY DETECTOR, AND X-RAY INSPECTION DEVICE

(71) Applicants: KABUSHIKI KAISHA TOSHIBA, Tokyo (JP); TOSHIBA MATERIALS CO., LTD., Yokohama-Shi (JP)

(72) Inventors: Hiroyasu Kondo, Yokohama (JP); Kazumitsu Morimoto, Yokohama (JP)

(73) Assignees: Kabushiki Kaisha Toshiba, Minato-Ku (JP); Toshiba Materials Co., Ltd., Yokohama-Shi (JP)

( * ) Notice: Subject to any disclaimer, the term of this patent is extended or adjusted under 35 U.S.C. 154(b) by 0 days.

(21) Appl. No.: 15/908,991

(22) Filed: Mar. 1, 2018

(65) Prior Publication Data

US 2018/0188386 A1 Jul. 5, 2018

Related U.S. Application Data

(63) Continuation of application No. PCT/JP2016/088050, filed on Dec. 21, 2016.

(30) Foreign Application Priority Data

Dec. 25, 2015 (JP) .................... 2015-254987

(51) Int. Cl.
*G01T 1/16* (2006.01)
*G01T 1/164* (2006.01)
(Continued)

(52) U.S. Cl.
CPC .......... *G01T 1/1644* (2013.01); *G01N 23/04* (2013.01); *G01T 1/2002* (2013.01);
(Continued)

(58) Field of Classification Search
CPC .... G01T 1/1644; G01T 1/2018; G01T 1/2023
See application file for complete search history.

(56) References Cited

U.S. PATENT DOCUMENTS

2005/0258369 A1* 11/2005 Wieczorek ............ G01T 1/1615
250/366
2014/0239195 A1 8/2014 Arimoto et al.
(Continued)

FOREIGN PATENT DOCUMENTS

JP S63-259485 A1 10/1988
JP 2001-330680 A1 11/2001
(Continued)

OTHER PUBLICATIONS

International Search Report and Written Opinion (Application No. PCT/JP2016/088050) dated Mar. 21, 2017.

*Primary Examiner* — Michael C Bryant
(74) *Attorney, Agent, or Firm* — Burr & Brown, PLLC

(57) ABSTRACT

A ceramic scintillator array of an embodiment includes: a plurality of scintillator segments each composed of a sintered compact of a rare earth oxysulfide phosphor; a first reflective layer interposed between the scintillator segments adjacent to each other; and a second reflective layer arranged on a side of surfaces, on which an X-ray is incident, of the plurality of scintillator segments. A difference in dimension between an end portion of a surface of the second reflective layer and a most convex portion of the surface of the second reflective layer is 30 μm or less.

8 Claims, 3 Drawing Sheets

(51) Int. Cl.
  *G01N 23/04*    (2018.01)
  *G21K 4/00*     (2006.01)
  *G01T 1/20*     (2006.01)
  *G01T 1/202*    (2006.01)
  *G01T 1/29*     (2006.01)
  *A61B 6/00*     (2006.01)
  *C09K 11/77*    (2006.01)

(52) U.S. Cl.
  CPC .......... *G01T 1/2018* (2013.01); *G01T 1/2023* (2013.01); *G01T 1/2985* (2013.01); *G21K 4/00* (2013.01); *A61B 6/40* (2013.01); *C09K 11/7713* (2013.01); *G21K 2004/06* (2013.01)

(56)　　　　　References Cited

U.S. PATENT DOCUMENTS

2014/0301527 A1\* 10/2014 Morimoto ............ G01N 23/046
　　　　　　　　　　　　　　　　　　　　　378/4
2015/0316660 A1 　11/2015 Arimoto et al.

FOREIGN PATENT DOCUMENTS

| JP | 2014-167405 A1 | 9/2014 |
| WO | 2013/080565 A1 | 6/2013 |

\* cited by examiner

CERAMIC SCINTILLATOR ARRAY, X-RAY DETECTOR, AND X-RAY INSPECTION DEVICE

CROSS-REFERENCE TO RELATED APPLICATIONS

This application is a continuation of prior International Application No. PCT/JP2016/088050, filed on Dec. 21, 2016 which is based upon and claims the benefit of priority from Japanese Patent Application No. 2015-254987, filed on Dec. 25, 2015; the entire contents of all of which are incorporated herein by reference.

FIELD

Embodiments described herein generally relate to a ceramic scintillator array, an X-ray detector, and an X-ray inspection device.

BACKGROUND

In fields of medical diagnosis, industrial non-destructive inspection and the like, inspection using an X-ray inspection device such as an X-ray tomograph (hereinafter, described as an X-ray CT scanner) is carried out. The X-ray CT scanner is composed of an X-ray tube (X-ray source) emitting a fan beam X-ray in a fan shape and an X-ray detector including many X-ray detection elements, the X-ray tube and the X-ray detector being arranged opposed each other with a tomographic surface of an inspection target set as a middle. In the X-ray CT scanner, the X-ray tube emits the fan beam X-ray while rotating with respect to the inspection target, and the X-ray detector collects absorption data on X-ray transmitted through the inspection target. Thereafter, the X-ray absorption data is analyzed by a computer, whereby a tomogram is reproduced. For the radiation detector of the X-ray CT scanner, a detection element using a solid scintillator is widely used. In the X-ray detector including the detection element using the solid scintillator, it is easy to increase the number of channels by downsizing the detection element, thus further increasing the resolution of the X-ray CT scanner and the like.

The X-ray inspection device such as the X-ray CT scanner is used in various fields for medical purpose, industrial purpose and so on. As the X-ray CT scanner, for example, there is a known device of a multi-splice type in which detection elements such as photodiodes are vertically and horizontally arranged in two dimensions and a scintillator array is mounted thereon. Employing the multi-splice type makes it possible to superpose cross-sectional images, thereby three-dimensionally expressing the CT image. The X-ray detector mounted in the X-ray inspection device includes detection elements arranged in a plurality of vertical and horizontal lines, and each of the detection elements is provided with a scintillator segment. The X-ray incident on the scintillator segment is converted into visible light, and the detection element converts the visible light into an electric signal to image it. In recent years, to obtain high resolution, the detection element is downsized and the pitch between adjacent detection elements is reduced. Accompanying the above, the size of the scintillator segment is also reduced.

Among the various kinds of scintillator materials used for the above-described scintillator segment, a rare earth oxysulfide-based phosphor ceramics is high in light emission efficiency and has preferable characteristics for use in the scintillator segment. Therefore, an X-ray detector is becoming widely used which is made by combining a ceramic scintillator segment processed by cutout process or grooving process from a sintered compact (ingot) of the rare earth oxysulfide-based phosphor ceramics being the scintillator material and a photodiode as the detection element.

As the scintillator using the phosphor ceramics, there is a known ceramic scintillator composed of a sintered compact of, for example, a gadolinium oxysulfide phosphor. The ceramic scintillator array is fabricated as follows for instance. First, the rare earth oxysulfide-based phosphor powder being the scintillator material is molded into a suitable shape, and the molded powder is sintered into a sintered compact (ingot). The sintered compact of the scintillator material is subjected to a cutting process such as cutout process or grooving process to form scintillator segments corresponding to the plurality of detection elements. A reflective layer is formed between the scintillator segments to integrate them, thereby fabricating the ceramic scintillator array. Further, the scintillator array is required to have a structure that confines light generated by the incident X-ray in the scintillator segments so as to prevent the light from passing through an X-ray incident surface and efficiently takes the light out to the photodiode side. To this end, a reflective layer is formed also on the X-ray incident surface of the ceramic scintillator array.

In the case of using the above-described ceramic scintillator array as the X-ray detector, the dimensional accuracy of the ceramic scintillator array affects the alignment accuracy when bonded to the photodiode and accordingly the resolution of an X-ray CT diagnostic image. Further, a temperature of 50° C. at maximum is applied to the X-ray detector mounted on the X-ray CT scanner. In the scintillator array having the reflective layer containing a resin, expansion of the reflective layer due to heating and contraction due to a decrease in temperature occur to cause a small dimensional change between adjacent scintillator segments, namely, pitch shift of the segment, warpage of the scintillator array, variation in outside dimension and so on. These become a cause of deteriorating the resolution of the diagnostic image of the X-ray detector. In progress of increase in resolution of the diagnostic image of the X-ray detector, a scintillator array having a smaller dimensional change amount due to heating and cooling is required. Further, since the area of the scintillator array also increases with an increase in detection area of the X-ray detector, the control of the dimensional change amount due to temperature change is important. In particular, the warpage of the scintillator array may cause not only a decrease in accuracy due to the dimensional change but also peeling of the reflective layer at the X-ray incident surface.

DETAILED DESCRIPTION

A ceramic scintillator array of an embodiment includes: a plurality of scintillator segments each composed of a sintered compact of a rare earth oxysulfide phosphor; a first reflective layer interposed between the scintillator segments adjacent to each other in a manner to integrate the plurality of scintillator segments; and a second reflective layer arranged on a side of surfaces, on which an X-ray is incident, of the plurality of scintillator segments. In the ceramic scintillator array of the embodiment, under a temperature environment of 50° C. or lower, a difference in dimension between an end portion of a surface of the second reflective layer and a most convex portion of the surface of the second reflective layer is 30 μm or less.

Hereinafter, embodiments for implementing a ceramic scintillator array, an X-ray detector, and an X-ray inspection device of the present invention will be described.

(Ceramic Scintillator Array)

Figure 1:
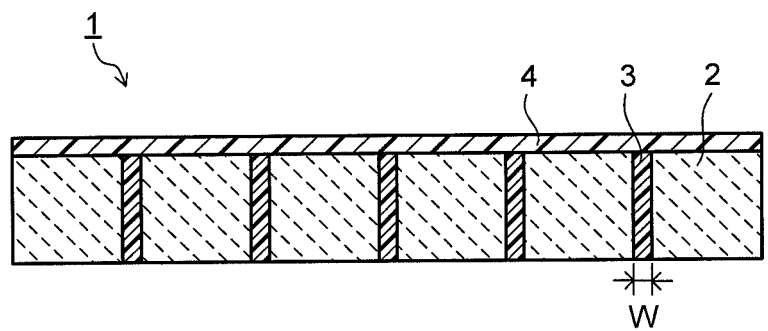
FIG. 1 is a cross-sectional view illustrating a ceramic scintillator array of an embodiment.
Figure 2:
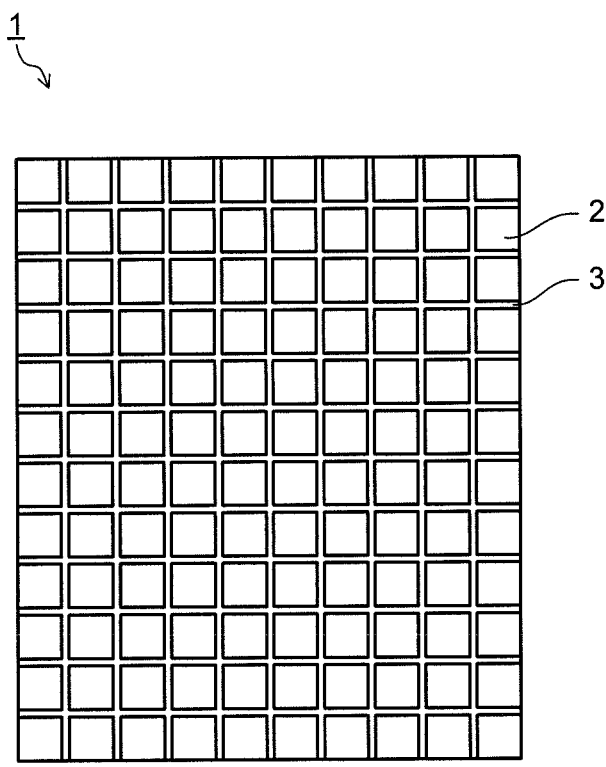
FIG. 2 is a plan view illustrating the ceramic scintillator array of the embodiment.

FIG. 1 is a cross-sectional view illustrating a ceramic scintillator array of an embodiment, and FIG. 2 is a plan view illustrating the ceramic scintillator array of the embodiment. In these drawings, 1 denote a scintillator array, 2 denotes a scintillator segment, 3 denotes a first reflective layer, and 4 denotes a second reflective layer. In FIG. 2, illustration of the second reflective layer 4 is omitted. The scintillator array 1 has a plurality of scintillator segments 2. Between adjacent scintillator segments 2, the first reflective layer 3 is interposed. The first reflective layer 3 is bonded to each of the adjacent scintillator segments 2. The plurality of scintillator segments 2 are integrated by the first reflective layers 3 bonded to them. In other words, the scintillator array 1 has a structure in which the plurality of scintillator segments 2 are integrated by the first reflective layers 3. Further, the second reflective layer 4 is provided on surfaces, on which an X-ray is incident, of the plurality of scintillator segments 2.

The scintillator array 1 may have any one of a structure in which the plurality of scintillator segments 2 are arranged in a line and a structure in which the plurality of scintillator segments 2 are arranged in two dimensions with a predetermined number of the scintillator segments 2 arranged each in a vertical direction and a horizontal direction as illustrated in FIG. 2. In the case where the plurality of scintillator segments 2 are arrayed in two dimensions, the first reflective layer 3 is provided between the scintillator segments 2 in each of the vertical direction and the horizontal direction. Further, the second reflective layer 4 is provided on X-ray incident surfaces of the plurality of scintillator segments 2 integrated via the first reflective layers 3. The second reflective layer 4 is bonded to each of the X-ray incident surfaces of the plurality of scintillator segments 2. The number of scintillator segments 2 is appropriately set according to the structure and resolution of the X-ray detector.

The scintillator segment 2 is composed of a sintered compact of a rare earth oxysulfide phosphor. An example of a rare earth oxysulfide phosphor ceramics is a rare earth oxysulfide phosphor containing praseodymium (Pr) as an activator. Examples of the rare earth oxysulfide constituting a phosphor ceramics include oxysulfides of rare earth elements such as yttrium (Y), gadolinium (Gd), lanthanum (La), lutetium (Lu) and so on.

The scintillator segment 2 in the ceramic scintillator array 1 of the embodiment is preferably composed of a rare earth oxysulfide phosphor ceramics (scintillator material) having a composition expressed by general formula:

$$RE_2O_2S:Pr \qquad (1)$$

where RE is at least one element selected from the group consisting of Y, Gd, La, and Lu.

Gd, in particular, of the above-described rare earth elements has a large X-ray absorption coefficient and contributes to improvement in light output of the ceramic scintillator array 1. Accordingly, it is more preferable to use $Gd_2O_2S:Pr$ phosphor for the scintillator segment 2 of the embodiment. Note that another rare earth element may substitute for a part of Gd. In this case, a substitution amount of another rare earth element for Gd is preferably set to 10 mol % or less.

More specifically, in the ceramic scintillator array 1 of the embodiment, it is desirable to use, for the scintillator segment 2, the rare earth oxysulfide phosphor ceramics substantially expressed by general formula:

$$(Gd_{1-x},RE'_x)_2O_2S:Pr \qquad (2)$$

where RE' is at least one element selected from the group consisting of Y, La, and Lu, and x is a number of atomic ratio satisfying 0≤x≤0.1.

In the ceramic scintillator array 1 of the embodiment, praseodymium (Pr) is used as the activator that increases light output of the rare earth oxysulfide phosphor ceramics (scintillator material). Pr can further reduce afterglow or the like as compared with other activators. Accordingly, the rare earth oxysulfide phosphor ceramics (scintillator material) containing Pr as the activator is effective as a fluorescence generating means of the radiation detector.

The content of Pr in the rare earth oxysulfide phosphor ceramics is preferably set to a range of 0.001 to 10 mol % relative to a phosphor host (for example, $RE_2O_2S$ such as $Gd_2O_2S$). A content of Pr exceeding 10 mol % conversely causes a decrease in light output. A content of Pr less than 0.001 mol % fails to provide sufficient effect as a main activator. The content of Pr is preferably in a range of 0.01 to 1 mol %.

In the rare earth oxysulfide phosphor ceramics used in the embodiment, a small amount of at least one element selected from the group consisting of Ce, Zr, and P may be contained as a coactivator in addition to Pr as the main activator. These elements exhibit effect to suppression of exposure deterioration, suppression of afterglow and so on. The contents of the coactivators are preferably set, as a total amount, to a range of 0.00001 to 0.1 mol % relative to the phosphor host.

Further, a scintillator sintered compact forming the scintillator segment 2 of the embodiment is preferably composed of a high-purity rare earth oxysulfide-based phosphor ceramics (scintillator material). Since impurities become a cause of a decrease in sensitivity of the scintillator, it is preferable to reduce as much as possible the impurity amount. In particular, a phosphate radical ($PO_4$) becomes a cause of a decrease in sensitivity, and therefore its content is preferably set to 150 ppm or less. In the case of using fluoride or the like as a sintering aid for densification, the sintering aid remains as an impurity, causing a decrease in sensitivity.

Figure 3:
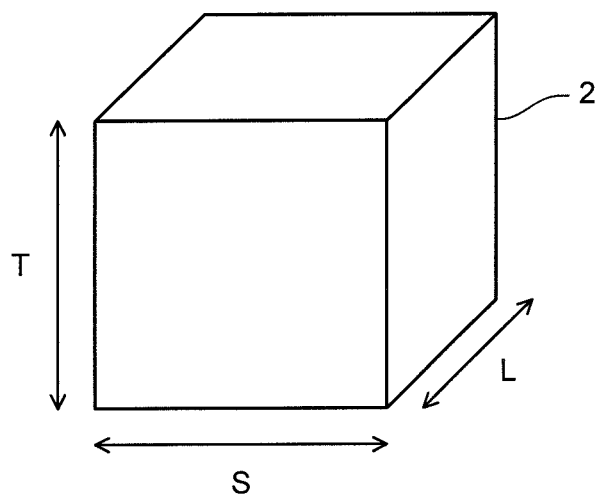
FIG. 3 is perspective view illustrating a scintillator segment used for the ceramic scintillator array of the embodiment.

The scintillator segment 2 is composed of a sintered compact in a cube shape or a rectangular parallelepiped shape as illustrated in FIG. 3. The volume of the scintillator segment 2 is preferably 1 $mm^3$ or less. Downsizing the scintillator segment 2 makes it possible to obtain an image to be detected with higher definition. Each size of the length (L), breadth (S) and thickness (T) of the scintillator segment 2 is not always limited, but is preferably 1 mm or less. When the volume of the scintillator segment 2 is downsized to be 1 $mm^3$ or less, the width (W) of the first reflective layer 3 can be made smaller to 100 or less, and further to 50 μm or less.

In the ceramic scintillator array 1 of the embodiment, the plurality of scintillator segments 2 are integrated via the first reflective layers 3, and the second reflective layer 4 is provided on the X-ray incident surfaces of the plurality of integrated scintillator segments 2. Under a temperature environment of 50° C. or lower being the use environment temperature of the ceramic scintillator array 1, a difference in dimension (warpage) between an end portion and a most convex portion of the surface (X-ray incident surface) of the second reflective layer 4 is 30 μm or less. The most convex portion of the second reflective layer 4 indicates a portion which exists at a position of the surface (X-ray incident surface) of the second reflective layer 4, farthest from a forming surface (reference plane) of the second reflective layer 4 on the plurality of scintillator segments 2.

Making the warpage amount of the second reflective layer 4 under the temperature environment of 50° C. or lower to 30 μm or less enables suppression of a decrease in accuracy due to a small dimensional change (pitch shift) between adjacent scintillator segments 2, dimensional change such as variation in outside dimension and so on, thereby improving the resolution of the diagnostic image by the X-ray detector. Further, peeling of the second reflective layer 4 can be suppressed. The warpage amount of the second reflective layer 4 under the temperature environment of 50° C. or lower is more preferably 20 μm or less. Further, the thickness of the second reflective layer 4 is preferably in a range of 50 to 250 μm. When the thickness of the second reflective layer 4 is less than 50 μm, sufficient effect of improving the reflection efficiency cannot be obtained in some cases. When the thickness of the second reflective layer 4 exceeds 250 μm, the X-ray amount transmitted decreases, resulting in a decrease in detection sensitivity.

In the ceramic scintillator array 1 of the embodiment, each of the first reflective layers 3 integrating the plurality of scintillator segments 2 and the second reflective layer 4 provided on the X-ray incident surfaces of the plurality of integrated scintillator segments 2 contains a transparent resin and reflective particles dispersed in the transparent resin. The reflective particles dispersed in the transparent resin in the first reflective layer 3 and the reflective particles dispersed in the transparent resin in the second reflective layer 4 are preferably particles of the same inorganic substance. It is preferable to use, as the reflective particles, particles of at least one inorganic substance selected from the group consisting of titanium oxide ($TiO_2$), alumina ($Al_2O_3$), barium sulfide ($BaSO_4$), and zinc oxide (ZnO). Using the reflective particles makes it possible to increase the reflectance by the reflective layers 3, 4 with respect to visible light emitted from the scintillator segments 2, and accordingly to increase light output of the scintillator array 1.

The reflective particles preferably have a bimodal-type particle size distribution. More specifically, the reflective particles preferably have a particle size distribution having a first particle diameter peak and a second particle diameter peak. Further, it is preferable that in the particle size distribution of the reflective particles, the first particle diameter peak exists in a range of 200 to 350 nm and the second particle diameter peak exists in a range of 750 to 1000 nm. In the case where the particle size distribution of the reflective particles is of a unimodal type, the reflection efficiency of the reflective layers 3, 4 with respect to light having a wavelength of 512 nm becomes more likely to decrease. In contrast to the above, using the reflective particles having the bimodal-type particle size distribution can increase the reflection efficiency of the reflective layers 3, 4. Specifically, the reflection efficiency of the reflective layers 3, 4 with respect to light having a wavelength of 512 nm is preferably 90% or more, with which the variation in light output of the ceramic scintillator array 1 can be reduced.

For the transparent resin constituting the second reflective layer 4, a resin having a glass transition point (transition temperature) of 30° C. or lower is preferably used. Since any of the temperature during process of manufacturing an X-ray CT scanner, the temperature during use of the X-ray CT scanner, and the temperature of a storage environment of the X-ray CT scanner is about 18 to 50° C., the expansion and contraction of the second reflective layer 4 during manufacturing process, during use, and during storage become easy as long as the glass transition point of the transparent resin constituting the second reflective layer 4 is 30° C. or lower, and thereby can suppress the warpage due to the thermal expansion coefficient difference between the second reflective layer 4 and the scintillator segment 2 and dimensional change (pitch shift of the segment, variation in outside dimension) based on the warpage, and the peeling of the second reflective layer 4. A glass transition point of the transparent resin constituting the second reflective layer 4 is preferably 20° C. or lower.

To satisfy the above-described glass transition point of 30° C. or lower, it is preferable to use a resin having a molecular structure including a double structure (double bond), as the transparent resin constituting the second reflective layer 4. In the case where the molecular structure of the transparent resin constituting the second reflective layer 4 does not include the double structure, the glass transition point is likely to exceed 30° C. The transparent resin constituting the second reflective layer 4 preferably includes at least one selected from the group consisting of an epoxy resin, a silicone resin, a phenol resin, a urea resin, a melamine resin, unsaturated polyester, polyurethane, an acrylic resin, and polyethylene terephthalate, and the molecular structure of the selected resin preferably includes the double structure.

For the transparent resin constituting the first reflective layer 3, a resin having a glass transition point of 50° C. or higher is preferably used. Since any of the temperature during process of manufacturing the X-ray CT scanner, the temperature during use of the X-ray CT scanner, and the temperature of the storage environment of the X-ray CT scanner is about 18 to 50° C., it is possible to suppress dimensional change (pitch shift of the segment, warpage of the scintillator array, variation in outside dimension) due to the expansion and contraction of the first reflective layer 3 during manufacturing process, during use, and during storage as long as the glass transition point of the transparent resin is 50° C. or higher. The glass transition point of the transparent resin constituting the first reflective layer 3 is more preferably 60° C. or higher, and furthermore preferably 85° C. or higher.

To satisfy the above-described glass transition point of 50° C. or higher, it is preferable to use a resin having a molecular structure including a cyclo structure including no double structure (double bond), as the transparent resin constituting the first reflective layer 3. In the case where the molecular structure of the transparent resin constituting the first reflective layer 3 includes the double structure, the glass transition point is likely to be lower than 50° C. The transparent resin constituting the first reflective layer 3 preferably includes at least one selected from the group consisting of an epoxy resin, a silicone resin, a phenol resin, a urea resin, a melamine resin, unsaturated polyester, polyurethane, an acrylic resin, and polyethylene terephthalate, and the molecular structure of the selected resin preferably includes the cyclo structure including no double structure.

Regarding the ratio between the transparent resin and the reflective particles forming the first reflective layer 3 and the second reflective layer 4, the mass ratio of the transparent resin is preferably 15 to 60%, and the mass ratio of the reflective particles is 40 to 85% (where the mass ratio of the transparent resin+the mass ratio of the reflective particles=100%). When the mass ratio of the reflective particles is less than 40%, the reflection efficiency of the reflective layers 3, 4 decreases, and the reflection efficiency of the reflective layers 3, 4 with respect to light having a wavelength of 512 nm is likely to be lower than 90%. When the mass ratio of the reflective particles exceeds 85%, the reflection efficiency of the reflective layers 3, 4 does not change, but the mass ratio of the transparent resin relatively decreases, possibly resulting in difficulty in stable solidification of the reflective layers 3, 4.

According to the ceramic scintillator array 1 using the above-described first reflective layer 3 and second reflective layer 4, the dimensional change amount due to the change in pitch of the segment, the change in warpage and outside dimension and so on can be suppressed. Accordingly, the ceramic scintillator array 1 with less variation in light output can be provided. Further, the decrease in light output of the ceramic scintillator array 1 can be suppressed.

The ceramic scintillator array 1 of the embodiment is manufactured as follows for instance. First, a mixture (first mixture) of the reflective particles and a resin composition in an uncured state constituting the transparent resin (an uncured material of the transparent resin) is prepared as a forming material for the first reflective layer 3. Then, a plurality of scintillator segments 2 each processed in a predetermined shape are arranged at regular intervals. The above-described first mixture of the reflective particles and the resin composition in the uncured state is applied or filled between adjacent scintillator segments 2. The resin composition in the uncured state preferably has a viscosity of 0.2 to 1 Pa·s. When the viscosity of the resin composition is less than 0.2 Pa·s, the flowability becomes low, resulting in deterioration of the workability of applying or filling between the scintillator segments 2. When the viscosity of the resin composition exceeds 1 Pa·s, the flowability becomes too high, resulting in a decreased in coating performance or filling performance. After the first mixture is applied or filled between the plurality of scintillator segments 2, the resin composition in the first mixture is cured to form the first reflective layer 3.

Then, a mixture (second mixture) of the reflective particles and a resin composition in an uncured state constituting the transparent resin (an uncured material of the transparent resin) is prepared as a forming material for the second reflective layer 4. The second mixture is applied on the X-ray incident surfaces of the plurality of scintillator segments 2 integrate via the first reflective layers 3. Thereafter, the resin composition in the second mixture is cured to form the second reflective layer 4, thereby manufacturing the ceramic scintillator array 1 in which adjacent scintillator segments 2 are bonded and integrated by the first reflective layer 3 and the second reflective layer 4 is formed on the X-ray incident surface of the integrated product. The curing processing of the first and second mixtures is appropriately set according to the kinds or the like of the resin composition in the uncured state and a curing agent. For example, in the case of a thermosetting resin composition, the curing reaction is promoted by performing thermal processing. The curing processing of the first and second mixtures may be performed separately or simultaneously.

(X-Ray Detector)

Figure 4:
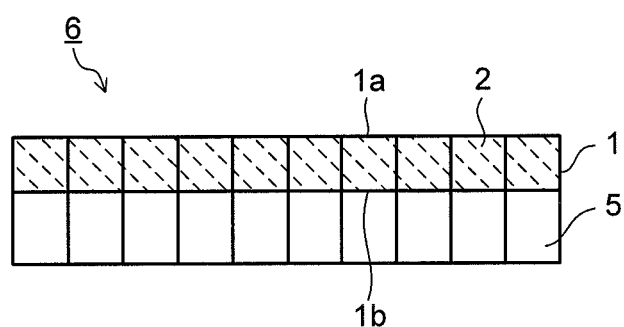
FIG. 4 is a view illustrating an X-ray detector of an embodiment.

The X-ray detector of an embodiment includes the above-described ceramic scintillator array 1 of the embodiment as a fluorescence generating means that emits light according to an incident radiation ray, and further includes a photoelectric conversion means that receives the light from the fluorescence generating means and converts the light output to an electric output. FIG. 4 illustrates an example of the X-ray detector of the embodiment. An X-ray detector 6 illustrated in FIG. 4 includes the ceramic scintillator array 1 as the fluorescence generating means and a photoelectric conversion element 5 like a photodiode as the photoelectric conversion means. In FIG. 4, illustration of the reflective layers 3, 4 of the ceramic scintillator array 1 is omitted.

The ceramic scintillator array 1 has an X-ray incident surface 1a, and the photoelectric conversion element 5 is integrally mounted on a surface 1b on the opposite side to the X-ray incident surface 1a. As the photoelectric conversion element 5, for example, a photodiode is used. The photoelectric conversion element 5 is arranged to correspond to each of the plurality of scintillator segments 2 constituting the ceramic scintillator array 1. They constitute the X-ray detector 6.

(X-Ray Inspection Device)

Figure 5:
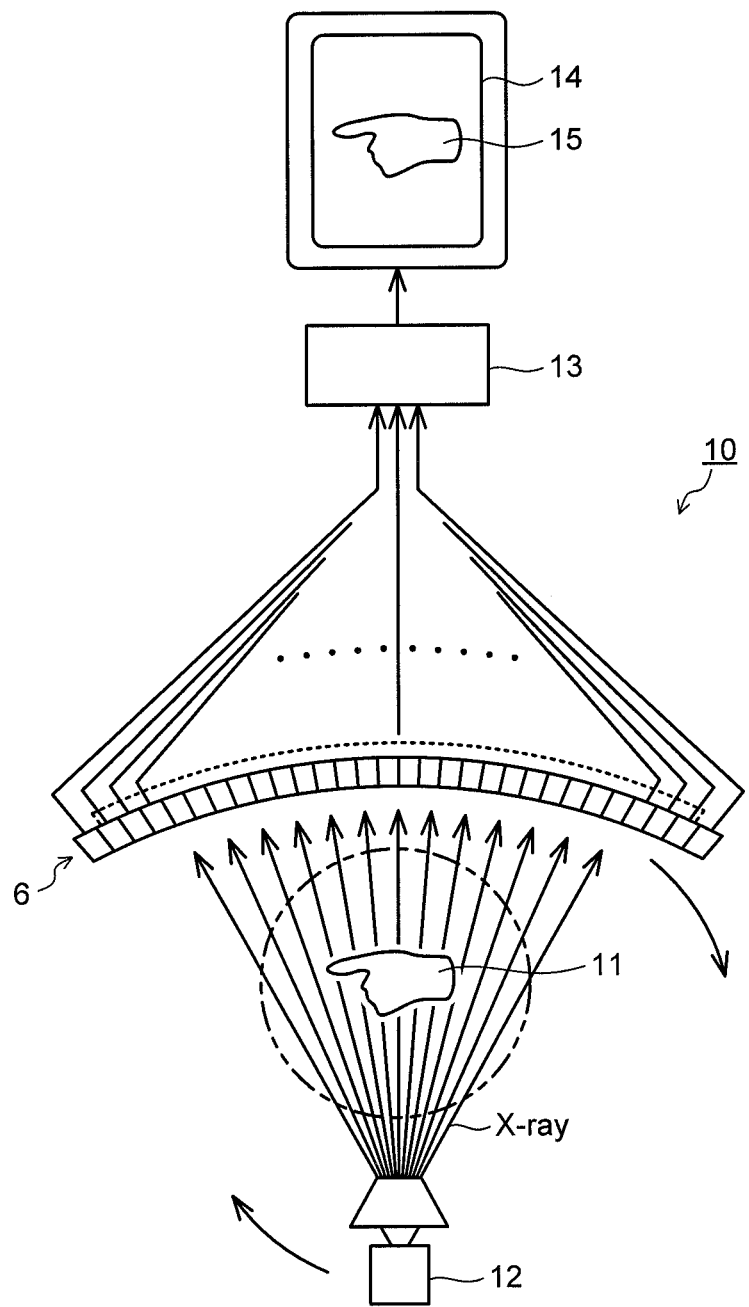
FIG. 5 is a view illustrating an X-ray inspection device of an embodiment.

The X-ray inspection device of an embodiment includes an X-ray source that emits an X-ray toward an inspection target, and an X-ray detector that detects the X-ray transmitted through the inspection target. For the X-ray detector, the above-described X-ray detector of the embodiment is used. FIG. 5 illustrates an X-ray CT scanner 10 being an example of the X-ray inspection device of the embodiment. In FIG. 5, 10 denotes an X-ray CT scanner, 11 denotes a specimen, 12 denotes an X-ray tube, 13 denotes a computer, 14 denotes a display, and 15 denotes a specimen image. The X-ray CT scanner 10 includes the X-ray detector 6 of the embodiment. The X-ray detector 6 is pasted on, for example, an inner wall surface of a cylinder where an imaged part of the specimen 11 is arranged. At an almost center of an arc of the cylinder where the X-ray detector 6 is pasted, the X-ray tube 12 that emits an X-ray is mounted. Between the X-ray detector 6 and the X-ray tube 12, the specimen 11 is arranged. On the X-ray incident surface side of the X-ray detector 6, a not-illustrated collimator is provided.

The X-ray detector 6 and the X-ray tube 12 are configured to rotate while photographing with the X-ray around the specimen 11. Image information on the specimen 11 is three-dimensionally collected from different angles. Signals obtained by X-ray photography (electric signals converted by the photoelectric conversion element) are processed by the computer 13 and displayed as the specimen image 15 on the display 14. The specimen image 15 is, for example, a tomogram of the specimen 11. Using the scintillator array 1 in which the scintillator segments 2 are two-dimensionally arranged as illustrated in FIG. 4 also makes it possible to constitute a multi-tomogram type X-ray CT scanner 10. In this case, a plurality of tomograms of the specimen 11 are photographed at the same time and, for example, a photographing result can be three-dimensionally drawn.

The X-ray CT scanner 10 illustrated in FIG. 5 includes the X-ray detector 6 including the ceramic scintillator array 1 of the embodiment. As described above, the ceramic scintillator array 1 of the embodiment has excellent light output because the reflection efficiency with respect to visible light emitted from the scintillator segments 2 is high on the basis of the configuration or the like of the reflective layers 3, 4.

Using the X-ray detector 6 including the scintillator array 1 makes it possible to shorten the photographing time by the X-ray CT scanner 10. As a result, it is possible to shorten the exposure time of the specimen 11 and achieve reduced exposure. The X-ray inspection device (X-ray CT scanner 10) of the embodiment is applicable not only to the X-ray inspection for medical diagnosis of a human body but also to the X-ray inspection for animals, the X-ray inspection for industrial usage and so on. Further, the X-ray inspection device also contributes to an improvement in inspection accuracy by an X-ray nondestructive inspection device.

EXAMPLES

Next, concrete examples of the present invention and their evaluation results will be described.

Examples 1 to 3, Comparative Examples 1 to 3

A phosphor powder having a composition of $Gd_2O_2S$:Pr (Pr concentration=0.05 mol %) was temporarily molded by rubber pressing, and a temporarily molded body was enclosed by deaeration in a capsule made of Ta and then set in an HIP processing apparatus. Into the HIP processing apparatus, an argon gas was sealed as a pressurizing medium, and processing was carried out for 3 hours under conditions of a pressure of 147 MPa and a temperature of 1425° C. In the above manner, a sintered compact in a cylindrical shape having a diameter of about 80 mm×a height of about 120 mm was fabricated. From the sintered compact, scintillator segments each having a thickness of 0.7 mm×a width of 0.7 mm×a length of 0.8 mm were cut in a matrix form of 100 segments in the length direction and 30 segments in the width direction.

The above-described plurality of scintillator segments were integrated via a first reflective layer composed of a mixture of 65 mass % of reflective particles and 35 mass % of transparent resin to fabricated an array-shaped product. A first reflective layer having a thickness of 0.1 mm was arranged in each of the vertical direction and the horizontal direction of the scintillator array. For the reflective particles, a mixture of 80 mass % of titanium oxide particles and 20 mass % of alumina particles was used. In Examples 1 to 3 and Comparative examples 1 to 3, hard epoxy resins A1 to A3 each having a molecular structure not including the double structure but including the cyclo structure were used for the transparent resins each forming the first reflective layer. The glass transition points of the hard epoxy resins A1 to A3 were adjusted by the molecular structures and are as listed in Table 1.

TABLE 1

| | Kind of Transparent Resin of First Reflective Layer | Molecular Structure | Glass Transition Point [° C.] |
|---|---|---|---|
| Example 1 | A1 | Cyclo Structure | 85 |
| Example 2 | A2 | Cyclo Structure | 65 |
| Example 3 | A3 | Cyclo Structure | 50 |
| Comparative Example 1 | A1 | Cyclo Structure | 85 |
| Comparative Example 2 | A2 | Cyclo Structure | 65 |
| Comparative Example 3 | A3 | Cyclo Structure | 50 |

The scintillator arrays according to examples and comparative examples were each fabricated by forming the second reflective layer on the X-ray incident surface of the array-shaped product made by integrating the plurality of scintillator segments via the first reflective layers. The thickness of the second reflective layer was set to 0.15 mm. For the reflective particles, a mixture of 80 mass % of titanium oxide particles and 20 mass % of alumina particles was used similarly to the first reflective layer. In Examples 1 to 3, soft epoxy resins B1 to B3 each having a molecular structure including the double structure were used for the transparent resins forming the second reflective layers. The glass transition points of the soft epoxy resins B1 to B3 were adjusted by the molecular structures and are as listed in Table 2. In Comparative examples 1 to 3, the same hard epoxy resins A1 to A3 as the transparent resins of the first reflective layers were used for the transparent resins forming the second reflective layers.

TABLE 2

| | Kind of Transparent Resin of Second Reflective Layer | Molecular Structure | Glass Transition Point [° C.] |
|---|---|---|---|
| Example 1 | B1 | Double Structure | 10 |
| Example 2 | B2 | Double Structure | 2 |
| Example 3 | B3 | Double Structure | 20 |
| Comparative Example 1 | A1 | Cyclo Structure | 85 |
| Comparative Example 2 | A2 | Cyclo Structure | 65 |
| Comparative Example 3 | A3 | Cyclo Structure | 50 |

For the scintillator arrays according to Examples 1 to 3 and Comparative examples 1 to 3, the warpage on the side of the surface where the second reflective layer was formed (the difference in dimension between an end portion and a most convex portion of the surface of the second reflective layer) was measured under a temperature environment of room temperature (25° C.). The warpage was measured using a laser-type 3D camera surface shape inspection device (manufactured by Taiyo Electric Co. LTD., model: SP3D-01). The presence or absence of peeling of the second reflective layer under the above-described temperature environment was investigated. Their results are listed in Table 3.

TABLE 3

| | Warpage [μm] | Occurrence of Peeling |
|---|---|---|
| Example 1 | 10 | Absence |
| Example 2 | 6 | Absence |
| Example 3 | 19 | Absence |
| Comparative Example 1 | 150 | Presence |
| Comparative Example 2 | 130 | Presence |
| Comparative Example 3 | 135 | Presence |

As listed in Table 3, it was confirmed that the warpage amount of each of the ceramic scintillator arrays in Examples 1 to 3 was smaller than those of Comparative examples 1 to 3 and was 30 μm or less. The ceramic scintillator array having the warpage amount can improve the dimensional accuracy to cope with downsizing of the detector and the like while maintaining excellent light output, and can also prevent peeling of the second reflective layer. Accordingly, it is possible to provide a ceramic scintillator array having an optimal dimensional accuracy and reliability in an operating temperature range of the X-ray inspection device such as the X-ray CT scanner. Using the ceramic scintillator array makes it possible to increase the resolution and the image accuracy and thereby provide an X-ray detector and an X-ray inspection device improved in medical diagnosis performance and non-destructive inspection accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes may be made without departing from the spirit of the inventions. The embodiments and modifications would fall within the scope and spirit of the inventions and fall within the inventions as set forth in accompanying claims and their equivalents.

What is claimed is:

1. A ceramic scintillator array comprising:
a plurality of scintillator segments each composed of a sintered compact of a rare earth oxysulfide phosphor;
a first reflective layer interposed between the scintillator segments adjacent to each other in a manner to integrate the plurality of scintillator segments, the first reflective layer comprising a first transparent resin and first reflective particles dispersed in the first transparent resin; and
a second reflective layer arranged on a side of surfaces on which an X-ray is incident of the plurality of scintillator segments, the second reflective layer comprising a second transparent resin and second reflective particles dispersed in the second transparent resin;
wherein a glass transition point of the first transparent resin is 60° C. or higher, and a molecular structure of the first transparent resin has a cyclo structure including no double bond,
wherein a glass transition point of the second transparent resin is 30° C. or lower, and a molecular structure of the second transparent resin has a double bond,
wherein the first reflective layer contains, by mass ratio, 15% or more and 60% or less of the first transparent resin and 40% or more and 85% or less of the first reflective particles, and
wherein the second reflective layer contains, by mass ratio, 15% or more and 60% or less of the second transparent resin and 40% or more and 85% or less of the second reflective particles.

2. The ceramic scintillator array according to claim 1, wherein
the second reflective particles are the same particles as the first reflective particles.

3. The ceramic scintillator array according to claim 1, wherein each of the first and second reflective particles include particles of at least one inorganic substance selected from the group consisting of titanium oxide, alumina, barium sulfide, and zinc oxide.

4. The ceramic scintillator array according to claim 1, wherein each of the first and second transparent resins contains at least one selected from the group consisting of an epoxy resin, a silicone resin, a phenol resin, a urea resin, a melamine resin, unsaturated polyester, polyurethane, an acrylic resin, and polyethylene terephthalate.

5. The ceramic scintillator array according to claim 1, wherein
the rare earth oxysulfide phosphor has a composition expressed by a general formula:

$$RE_2O_2S:Pr,$$

wherein RE is at least one selected from the group consisting of Y, Gd, La, and Lu, and a content of Pr relative to $RE_2O_2S$ is 0.001 mol % or more and 10 mol % or less.

6. The ceramic scintillator array according to claim 5, wherein
the rare earth oxysulfide phosphor contains a gadolinium oxysulfide phosphor containing Pr as an activator.

7. An X-ray detector comprising the ceramic scintillator array according to claim 1.

8. An X-ray inspection device comprising the X-ray detector according to claim 7.

* * * * *